US007425208B1

(12) United States Patent
Vitello

(10) Patent No.: US 7,425,208 B1
(45) Date of Patent: Sep. 16, 2008

(54) NEEDLE ASSEMBLY FACILITATING COMPLETE REMOVAL OR NEARLY COMPLETE REMOVAL OF A COMPOSITION FROM A CONTAINER

(76) Inventor: Jonathan J. Vitello, 2881 W. McNab Rd., Pompano Beach, FL (US) 33069

( * ) Notice: Subject to any disclaimer, the term of this patent is extended or adjusted under 35 U.S.C. 154(b) by 511 days.

(21) Appl. No.: 10/651,603

(22) Filed: Aug. 29, 2003

(51) Int. Cl.
*A61B 19/00* (2006.01)
*A61M 5/32* (2006.01)

(52) U.S. Cl. ...................................... 604/411; 604/905

(58) Field of Classification Search ................. 604/122, 604/126, 181, 183, 239, 264, 174, 177, 272, 604/411, 414, 905; 600/573
See application file for complete search history.

(56) References Cited

U.S. PATENT DOCUMENTS 3,706,307 A 12/1972 Hasson
3,905,375 A 9/1975 Toyama
4,216,585 A 8/1980 Hatter
4,743,231 A 5/1988 Kay et al.
4,760,847 A 8/1988 Vaillancourt
5,049,129 A * 9/1991 Zdeb et al. .................... 604/85
5,356,380 A 10/1994 Hoekwater et al.
5,549,571 A 8/1996 Sak
5,776,124 A 7/1998 Wald
5,902,269 A 5/1999 Jentzen
5,951,522 A 9/1999 Rosato et al.
5,951,525 A 9/1999 Thorne et al.
6,021,824 A * 2/2000 Larsen et al. ............... 141/329
6,322,543 B1 11/2001 Singh et al.
6,375,640 B1 4/2002 Teraoka
6,500,155 B2 12/2002 Sasso
6,540,697 B2 * 4/2003 Chen .......................... 600/576
2002/0023409 A1 * 2/2002 Py ............................. 53/426

* cited by examiner

*Primary Examiner*—Kevin C. Sirmons
*Assistant Examiner*—Bhisma Mehta
(74) *Attorney, Agent, or Firm*—Malloy & Malloy, P.A.

(57) ABSTRACT

A needle assembly structured to facilitate substantially complete removal, if not the complete removal, of a pharmaceutical or other composition from a vial or like container. The needle assembly comprises a delivery needle having an elongated first portion of sufficient length to extend within and along the entire length of the interior of the vial. A distal end of the delivery needle is disposable in confronting engagement with an interior floor portion of the vial. The delivery needle is connected to a base and is concurrently movable relative thereto while maintaining the distal end of the first portion in confronting relation to the vial floor. Complete removal of the pharmaceutical composition from the vial is thereby facilitated.

9 Claims, 3 Drawing Sheets

NEEDLE ASSEMBLY FACILITATING COMPLETE REMOVAL OR NEARLY COMPLETE REMOVAL OF A COMPOSITION FROM A CONTAINER

BACKGROUND OF THE INVENTION

1. Field of the Invention

This invention relates to a needle assembly structured to facilitate substantially complete removal, if not entirely complete removal of a pharmaceutical or other fluid composition from the interior of a vial or like container. The needle assembly of this invention is structured to permit the selective adjustment of its cooperative components relative to one another as the needle assembly is oriented for extraction of the composition.

2. Description of the Related Art

The administration of a pharmaceutical composition to a patient by injection frequently requires the transfer of the pharmaceutical from a vial or like container into a syringe or like instrument. In doing so, a typical procedure involves forcing a sharpened tip of the needle of the syringe into the interior of the vial and into fluid communication with the pharmaceutical composition contained therein. In some instances, the vial is then inverted while adjusting the position of the needle to assure that the open receiving tip of the needle is submerged within the composition. An intended dose or measure of the pharmaceutical composition is then withdrawn from the vial and deposited into the barrel of the syringe. As commonly practiced, the above described extraction procedure requires an individual to closely monitor the position of the needle to assure that it remains submerged within the medication being extracted. This is to prevent excess air from being inadvertently drawn into the barrel of the syringe. However, when practicing the above-noted procedure, it is extremely difficult to remove substantially all of the medication from the vial, especially the last remnants thereof, which may collect at various hard to reach areas within the vial.

While there are some pharmaceutical compositions which, by their nature, allow for the vial to be opened in order that the last remnants thereof may be collected and used, there are others used in the modern day practice of medicine which are hazardous to humans, and which are not at all suitable for this. For example, certain pharmaceutical compositions such as, but not limited to radioactive pharmaceuticals are carcinogens and must be safely stored in lead-free containers, etc. Some of these and/or other pharmaceuticals must be stored under sterile conditions, such that the vials containing such pharmaceuticals cannot be opened or manipulated freely to remove all drops or remnants of them left collecting at the bottom of a vial. To compound this situation, these and other pharmaceutical compositions are often extremely expensive, and as such, it is important that all or substantially all of the composition be extracted and used.

As such various attempts have been made to address these problems and to improve the extraction procedure. For example, one known attempt involves the use of special extraction needles which are generally larger and otherwise structured to facilitate removal of the composition. However, such extraction needles and the syringes associated therewith may not be structured nor adaptable to inject the pharmaceutical directly into a patient or other intended target. More specifically, larger syringes and associated needles cannot be used to accurately dispense relatively small dosages of medicines directly into a patient or other intended target. Further, the vials associated with such pharmaceuticals often have an irregular, inner bottom or floor surface, and as such, conventional extraction instruments are not effectively capable of positioning the distal receiving end of the extraction needle into communication with the last remnants of the composition being removed.

Therefore, there is a significant and long recognized need in the field of art relating to the dispensing of pharmaceutical compositions for a needle assembly having the structural and operational versatility to effectively remove substantially all, if not all of a given composition from a container, especially when the size of the container, as well as the quantity of composition being removed, may vary greatly. Further, in accomplishing complete or substantially complete removal of the composition from a container, any such needle assembly developed should be capable of being selectively disposed into an operative position in a stable and reliable manner and should be further structured to prevent contamination of the composition during removal thereof from the container.

SUMMARY OF THE INVENTION

The present invention is intended to present a solution to these and other needs in the art, and as such, is directed to a needle assembly structured to facilitate the removal of substantially all, if not all, of a pharmaceutical composition, or other fluid from the interior of a vial or other type of container. As set forth above, certain radioactive pharmaceuticals are extremely expensive, and as such, their complete removal from a container is economically important. It is also important for these and other reasons to remove an accurate amount of a pharmaceutical composition from a container in order to deliver a prescribed dosage to a patient or other intended target. There are, of course, other reasons as to why it may be important that the entire quantity of a pharmaceutical composition be removed from a vial or other container in which it is supplied.

Therefore, the present invention is directed to a needle assembly that is structured to be selectively adjustable into an operative position relative to a vial or other container. The operative position is at least partially defined by orienting a delivery needle, as part of the needle assembly, relative to a floor or base of the vial so as to remove substantially all, if not all, of the quantity of contained pharmaceutical or other composition from the container. In the preferred embodiment, the delivery needle includes a first portion having a longitudinal dimension greater than that of the containment vial and being of sufficient length to extend along substantially the entire interior length of the vial when disposed therein. Further, the first portion includes an open, receiving, distal end disposable in confronting engagement with the base or floor portion of the vial. In such a position, the distal end will be disposed in fluid communication with the contained composition at a location which is immediately adjacent to or contiguous with the lower most interior portions of the vial, when the vial is disposed in a normally upright position, as intended. As a result, the distal end of the first portion of the delivery needle will be disposed in receiving relation with any remnants of the composition, after the vast majority of the composition has been removed from the vial.

As should be apparent, the structure and selective positioning of the first portion of the delivery needle in confronting relation to the floor of the vial will also serve to overcome any irregular structural configurations of the vial floor. It is commonly recognized that the configuration and/or overall structure of the interior surface of the base of pharmaceutical vials, especially when made of glass, are not consistently flat. Frequently, such surfaces are upwardly beveled, facilitating the collection of the pharmaceutical composition contained within the vial, especially if it is a liquid, to pool or collect in recesses and/or about the outer peripheral border of the floor or base. Therefore, selective orientation of the distal end of the delivery needle, preferably in the manner to be described hereinafter, is necessary in accomplishing complete removal of the contained composition.

Disposal of the first portion of the delivery needle in the aforementioned operative position is further facilitated by the provision of a base. The base includes a passage assembly structured to movably receive the delivery needle therein. Moreover, the delivery needle is selectively movable within the passage assembly and relative to the base, thereby allowing a user to selectively orient the distal end of the needle in the aforementioned, confronting relation to the interior container floor. Once the needle assembly is in the preferred operative position, the contents of the vial are removed from the interior thereof, while the vial is maintained in an upright, as versus inverted, position.

The delivery needle also includes a second portion communicating with the first portion to define a path of fluid flow of the composition as it is extracted from the vial interior. The second portion has an open proximal end, which may be connected to a luer fitting or other coupling structure for connection to a syringe or other extraction instrument. In at least one preferred embodiment, to be described in greater detail hereinafter, the first and second portions of the delivery needle are fixedly connected to one another, such that both are concurrently movable relative to the base. Accurate orientation of the needle assembly in the preferred operative position is further facilitated through the provision of a stop structure mounted on the base preferably in direct association with the passage way. The stop structure is disposable into movement restricting engagement with the delivery needle such that axial movement thereof in at least one direction is limited. As will also be explained more in detail herein, the stop structure may assume a variety of different structural configurations such that it is disposable in engagement with one or more portions of the delivery needle in order to limit travel or movement of the delivery needle relative to the base in either of two opposite directions.

Other structural features associated with the needle assembly of the present invention include the provision of a vent assembly. The vent assembly most preferably is in the form of a vent needle disposed to establish fluid communication between interior and exterior portions of the container. In order to prevent contamination, the vent assembly may further include a filter associated therewith. When utilized, the filter is disposed to filter fluid, particularly gasses, passing through the vent assembly between the interior and exterior of the container.

In view of the foregoing, it should be apparent that the needle assembly of the present invention facilitates removal of substantially all, if not all, of a given pharmaceutical or other fluid composition from the interior of a vial or like container through the disposition of an open, receiving distal end of a delivery needle into confronting engagement with the floor of the vial or container. Further, the needle assembly and in particular, the first portion of the delivery needle may be selectively positionable relative to the floor so as to further dispose the distal end of the first portion into direct communication with any remnants which may be collected in hard to reach areas on the interior of the container, such as due to an irregular configuration of the floor portion thereof.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT(S)

As shown in the accompanying drawings, the present invention is directed to a needle assembly generally indicated as 10 which is structured to facilitate the removal of substantially all, if not all, of a composition, such as but not limited to a pharmaceutical composition in liquid form, from the interior of a vial or other container, generally indicated as 12. As recited previously herein, it is well known that certain pharmaceuticals, such as those that are radioactive, are extremely expensive, and as such, it is important that all or nearly all of the pharmaceutical contained within a container be extracted for use.

As also recited previously herein, it is equally well recognized that the removal of all remnants of such pharmaceuticals from a vial or other container is not easily accomplished utilizing conventional needle assemblies or extraction equipment presently available. The extraction procedure is made more difficult by the fact that the interior configuration of containment vials, especially those made of glass, vary between production lots and are not produced with reliable structural consistency. Therefore, it is common for the interior surface of the base or floor 14 of the container 12 to have a configuration which makes it difficult, if not impossible, to position a conventional extraction needle on the interior of the container in a position to completely remove the pharmaceutical composition therefrom.

Figure 2:
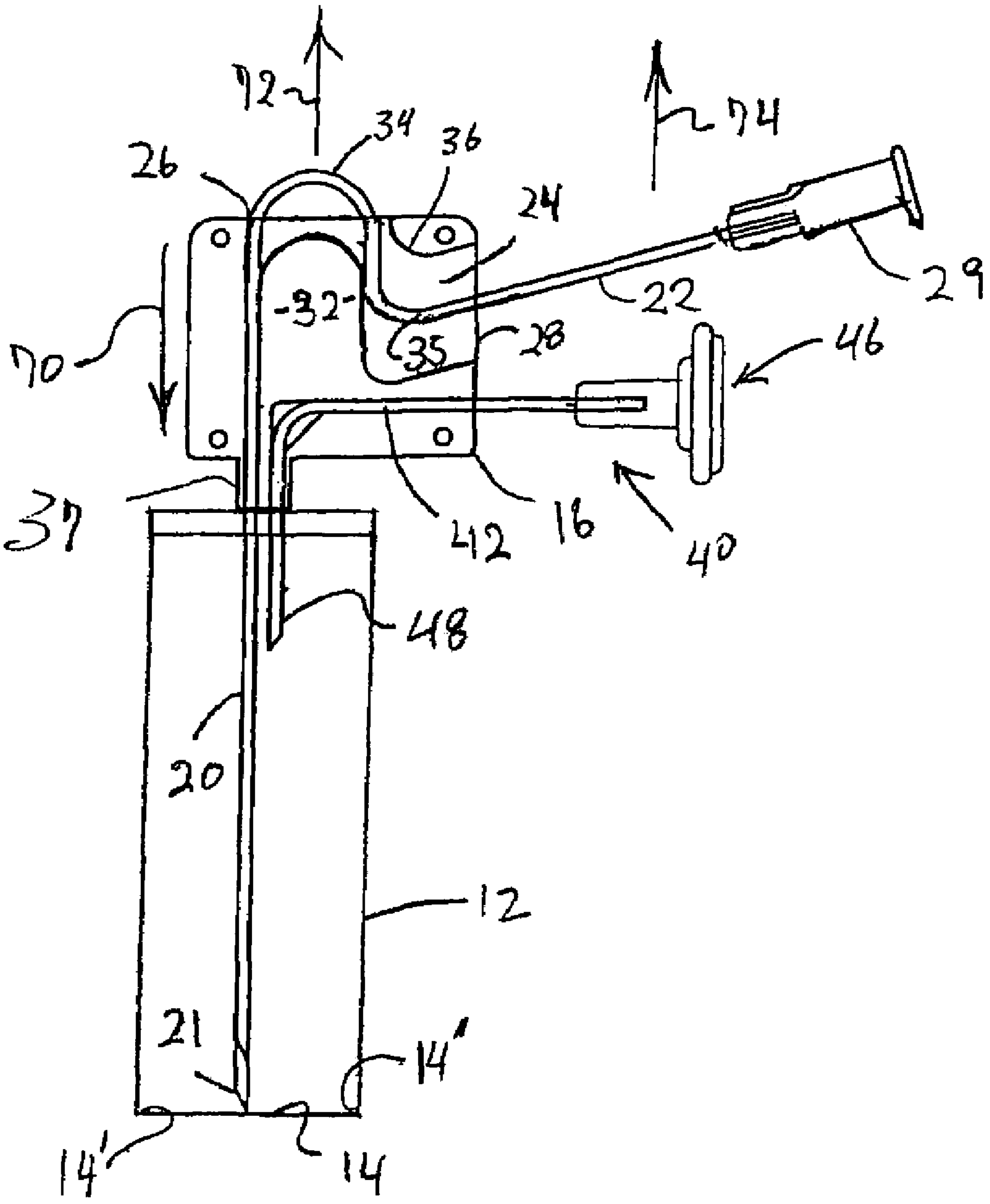
FIG. 2 is a similar view of the invention shown in FIG. 1, but illustrating the needle assembly in an operative position for removal of a pharmaceutical composition from the container.

Accordingly, the needle assembly 10 of the present invention is selectively disposable into a preferred operative position, as disclosed in FIG. 2, by the selective and adjustable manipulation of its operative components relative to one another. At the same time, the structure of the present invention preferably allows for the stability of the needle assembly 10, relative to the vial or container 12, to be reliably maintained during the extraction procedure.

Figure 1:
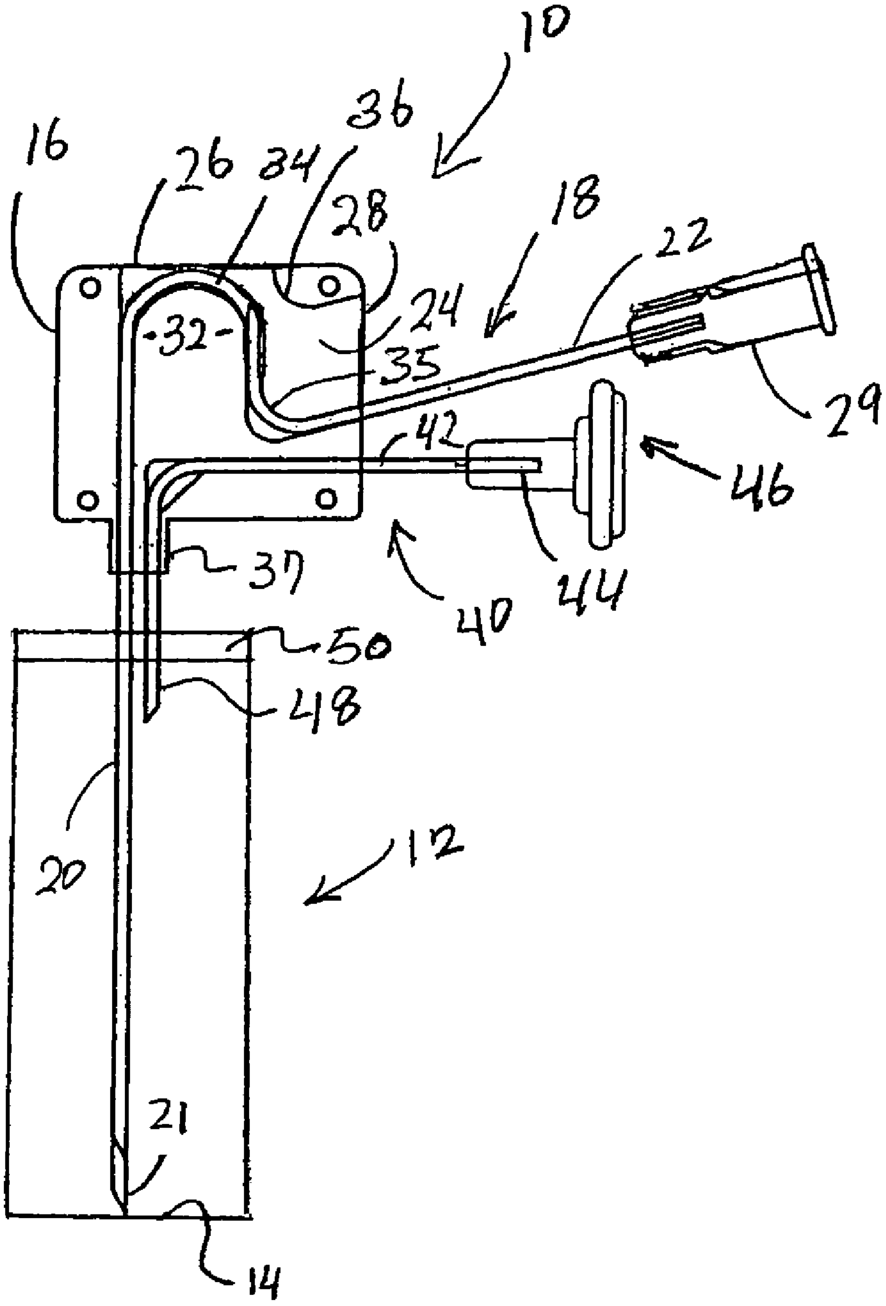
FIG. 1 is a side view of the needle assembly of the present invention in partial cross-section, and illustrating the assembly an introductory position relative to a vial or container, which is represented in schematic form.
Figure 4:
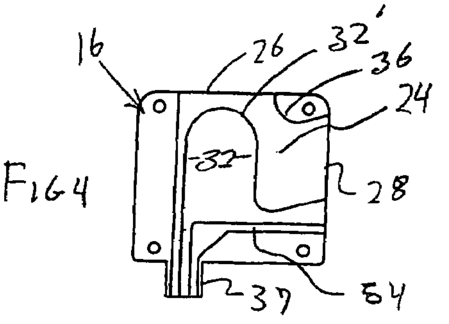
FIG. 4 is an isolated view showing interior portions of a preferred base associated with the embodiment of FIGS. 1 and 2.
Figure 5:
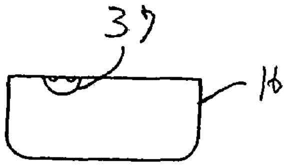
FIG. 5 is an end view of the embodiment of FIG. 4.
Figure 6:
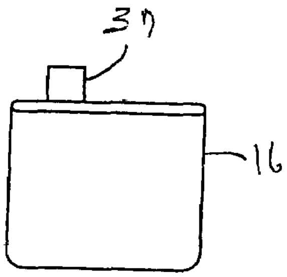
FIG. 6 is an exterior rear view of the embodiment of FIGS. 4 and 5.

With reference to FIGS. 1 and 2, the needle assembly 10 illustrated therein comprises a base 16 having a delivery needle generally indicated as 18 which is movably and adjustably connected thereto. The delivery needle 18 includes a first portion 20 intended to be disposed within the interior of the container 12 and a second portion 22 disposed on the exterior of the container 12, as demonstrated in FIGS. 1 and 2, and also in FIG. 3. For purposes of clarity, the base 16 as represented in FIGS. 1, 2 and 4 is broken away to show certain preferred interior structural features thereof, and the movable placement of at least the delivery needle 18 relative thereto. Therefore, at least one preferred embodiment of the present invention comprises the base 16 including a passage assembly 24 having two spaced apart openings 26 and 28 which are each disposed in communicating relation with an exterior of the base 16. Additional structural details of the base 16 are shown in FIGS. 5 and 6. When completely assembled, there is preferably a cover, shell or similarly structured opposite half or casing segment (not shown) disposed in overlying or covering relation to base 16, as represented in FIG. 4. The passage assembly 24 is thereby substantially enclosed other than the aforementioned openings 26 and 28. Attachment of the cover or opposite casing segment may be accomplished in any appropriate manner such as by heat welding, bonding, use of an adhesive, etc.

Figure 3:
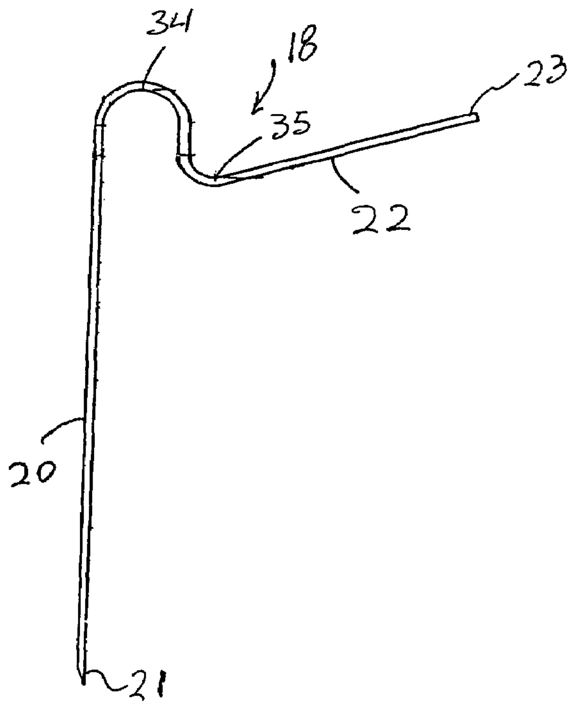
FIG. 3 is a isolated view of a preferred delivery needle comprising a portion of the needle assembly of the present invention.

Referring now to FIGS. 1 through 3, the delivery needle 18 includes a first portion 20 having a sufficient longitudinal dimension to extend along substantially the entire interior length of the vial or container 12. Further, the length of the first portion 20 is preferably greater than the length of the entire vial 12. As is recognized, the vial or like container 12 may be available in a variety of different standard sizes such as 10 cc, 20 cc, 30 cc, etc. In order to accommodate varying dimensions and different sizes of the vial 12, the needle assembly 10 may also be available in a variety of different sizes. However, the overall structure of the needle assembly 10 may be sufficient to accommodate more than one standard size of a vial or like container 12 and still be capable of extracting substantially all of the liquid pharmaceutical or like composition from the interior thereof.

In at least one preferred embodiment of the present invention, the delivery needle 18 includes the first and second portions 20 and 22 being integrally secured to one another so as to move together within the passage assembly 24, relative to the base 16. Moreover, the second portion 22 of the delivery needle 18 may extend outwardly in substantially transverse relation to the first portion 20. Also, the first portion 20 includes an open, fluid receiving distal end 21. Similarly, the second portion 22 includes an open proximal end 23 to which an appropriate structure, such as but not limited to a luer lock coupling 29, may be connected. The coupling 29 is of the type structured for connection to a syringe or other fluid extraction instrument to facilitate the removal of the composition from the container 12. Moreover, the delivery needle 18 comprises a path of fluid flow at least partially defined by the composition passing into the open distal end 21, through the interiors of the first portion 20 and the second portion 22 and out through the proximal end 23 and coupling 29.

In order to assure accurate positioning of the delivery needle 18 relative to the base, the passage assembly 24 preferably also includes a stop structure, including at least one stop member 32. The stop member 32 is disposed in restricting engagement with a first intermediate segment 34 of the delivery needle 18, as clearly represented in FIGS. 1 thorough 3. Being so positioned, the stop member 32 serves to restrict or limit the axial travel or movement of the first portion 20 relative to the base 16 as it extends outwardly from the hub 37 of the base 16. It should be noted that as shown in FIG. 4, an exposed peripheral surface 32' of the stop member 32 substantially corresponds to the arcuate or curvilinear configuration of the first intermediate segment 34 of the delivery needle 18. However, it is emphasized that the corresponding configurations of the peripheral surface 32' and the intermediate segment 34 may vary greatly from that disclosed and still accomplish the restricting engagement between the stop member 32 and the intermediate segment 34.

It is also to be noted that in at least one preferred embodiment of the present invention, the stop structure associated with the passage assembly 24 may include the aforementioned stop member 32, as well as a secondary stop member 36, as shown in FIGS. 1, 2 and 4. As such, the outward travel of the delivery needle 18 through the opening 26 of the passage way 24 is accomplished by a restricting engagement between the auxiliary stop member 36 and another or second intermediate needle segment 35. As disclosed in FIGS. 1 and 3, the other intermediate segment 35 is located substantially at the opposite end of the second portion 22 relative to the open proximal end 23. Therefore, in at least one preferred embodiment of the needle assembly 10, the delivery needle 18 is limited in its movement within the passage assembly 24 in oppositely disposed directions defined by the intermediate segment 34 engaging the stop member 32 or the other intermediate segment 35 engaging the auxiliary stop member 36, as at least partially demonstrated respectively in FIGS. 1 and 2.

Other structural features included in a most preferred embodiment of the needle assembly 10 includes a vent assembly, generally indicated as 40. The vent assembly 40 includes a vent needle 42 having an outer end 44 connected to a filter assembly generally indicated as 46. The filter assembly 46 may be sufficiently dimensioned and structured to filter gas or fluids passing through the filter needle 42. As such, it may preferably include a dimension of 0.2 microns in order to prevent contamination of the pharmaceutical composition contained within the vial 12. Naturally, the filter assembly 46 may come in a variety of other dimensions depending upon the particular pharmaceutical or other composition contained within the container 12. The opposite or interior end 48 of the vent needle 42 is disposed in direct fluid communication with the interior of the vial 12. Moreover, it is preferably disposed in spaced but substantially adjacent relation to the penetrable stopper or cover member 50 associated with the vial 12. The vent assembly 40 travels with the base 16 as the needle assembly 10 is disposed between the introductory position of FIG. 1 and the operative position of FIG. 2. As such, the vent needle 42 is fixedly secured to the base 16 in spaced relation to and substantially independently of the delivery needle 18. Therefore, the vent needle 42 may be secured within and/or connected to a secondary passage 54 formed in the base 16 in spaced relation to passage assembly 24.

In order to more fully emphasize the structural and operational versatility of the needle assembly 10, the placement thereof between the introductory position of FIG. 1 and the operative position of FIG. 2 will now be described. However, in explaining the extraction procedure and the selective positioning of the needle assembly 10, it will be noted that a syringe, conduit or other extraction instrumentation may be attached to the coupling 29, but is not shown. Such extraction equipment would be connected to the coupling 29 or otherwise connected in communicating relation with the delivery needle 18 in order to provide sufficient negative pressure or suction to withdraw the pharmaceutical or other composition from the interior of the container 12.

When it is intended to remove the composition from the interior of the container 12, the needle assembly 10 is disposed in the introductory position of FIG. 1. In such position, the delivery needle 18 is positioned relative to the base 16 such that the stop member 32 is disposed in restricting engagement with the intermediate portion 34. In such an orientation, the first portion 20 of the delivery needle 18 extends its maximum distance outwardly from the base 16, as the sharpened distal end 21 penetrates the closure or stopper 50 of vial 12. As set forth above, the length of the first portion 20 should be sufficient to extend along entire length of the interior of the vial 12 as it passes through the stopper 50 of the vial 12. The vent needle 42 is cooperatively dimensioned with the first portion 20, such that upon confronting engagement of the distal end 21 with the floor 14, the interior end 48 of the vent needle 42 will have penetrated the stopper 50 and be located on the interior of the container 12. Due to the ability to adjustably and relatively position the delivery needle 18 and base 16, once the distal end 21 of first portion 20 confronts the floor 14, the base 16 may be moved downwardly towards the vial 12 and into stable engagement between the hub 37 and the stopper or closure 50. Movement of the base 16 relative to the first portion 20 of the delivery needle 18 is indicated by directional arrow 70, shown in FIG. 2. Concurrently, the intermediate segment 34 moves outwardly from the base 16 through the opening 26, as the intermediate segment 34 is removed from the stop member 32, as indicated by directional arrow 72, also shown in FIG. 2. Due to the fixed or integral connection between the first portion 20 and the second portion 22 of the delivery needle 18, the second portion 22 travels transversely through the opening 28 and within the passageway 24 along with the first portion 20, as indicated by directional arrow 74 as also shown in FIG. 2.

While not specifically disclosed, it should be noted that the outward travel or movement of the delivery needle 18 relative to the base, as indicated by directional arrows 72 and 74 in FIG. 2, will be limited or restricted upon engagement of the auxiliary stop member 36 with the other intermediate portion 35. Therefore, a most preferred embodiment of the present invention comprises the delivery needle 18 including both the first and second portions 20 and 22, respectively, having the movement thereof relative to the base 16 being substantially restricted in both of two opposite directions. It should be apparent that the relative longitudinal dimensions of the vial 12 and the first portion 20 will be at least partially determinative of the forced travel of the delivery needle 18 a sufficient distance outwardly from the base 16, to the extent where the auxiliary stop member 36 engages the intermediate segment 35. More specifically, if the length of the container 12 is significantly less than that shown in FIGS. 1 and 2 downward movement of the base 16, in accord with directional arrow 70, as the distal end 21 contacts the floor 14, may cause a restricting engagement between the intermediate segment 35 and the auxiliary stop member 36.

Once in the operative position of FIG. 2, extraction of the entire quantity of pharmaceutical or other composition or nearly so, from the interior of the vial 12 is facilitated. It is further noted that the structure of the needle assembly 10 is such as to allow a selective lateral movement of the distal tip 21 relative to the floor 14, in order to further facilitate removal of substantially all, if not all, of the composition from the interior of the vial 12. Such selective lateral positioning may include the distal tip 21 being disposed into the peripheral corners or crevasses 14', as illustrated in FIG. 2.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A needle assembly structured to facilitate at least substantially complete removal of a composition from a container, said needle assembly comprising:

a) a base movable exteriorly of the container, b) a delivery needle including a first portion and a second portion, and a first intermediate portion and a second intermediate portion disposed in interconnecting relation to said first and second portions, c) said first portion being of sufficient length to extend into and along substantially an entire interior length of the container, d) said second portion connected in substantially transverse relation to said first portion and movable therewith, said second portion disposed exteriorly of the container, e) a passage assembly formed in said base, said passage assembly disposed and structured to allow axial movement of said first portion and transverse movement of said second portion through corresponding portions of said passage assembly, f) a stop structure including a first stop member and a secondary stop member disposed within said passage assembly in spaced relation to one another, g) said first intermediate portion movable through and within said passage assembly into and out of movement restricting engagement with said first stop member, h) said second intermediate portion movable through and within said passage assembly into and out of movement restricting engagement with said secondary stop member, and i) a vent assembly including a vent needle fixedly secured to said base and movable therewith relative to the container, said vent needle including a distal tip disposed interiorly of the container and a proximal end disposed exteriorly of the container.

2. A needle assembly as recited in claim 1 further comprising said passage assembly formed on said base, said first portion movable in an axial direction through said passage assembly and second portions movable through said passage assembly in a transverse direction relative to said base.

3. A needle assembly as recited in claim 1 further comprising a filter structure disposed adjacent said proximal end of said vent needle and structured to filter gas passing through said vent needle.

4. A needle assembly as recited in claim 1 wherein said vent needle comprises a substantially angular configuration.

5. A needle assembly as recited in claim 1 wherein said first stop member is disposed to prevent axial movement of said first portion through said passage assembly in a first direction when said first portion is disposed into engagement with said first stop member.

6. A needle assembly as recited in claim 5 wherein said secondary stop member is disposed to prevent axial movement of said first portion in a second direction, opposite to said first direction, and concurrently prevent transverse movement of said second portion within and through said passage assembly in said second direction.

7. A needle assembly structured to facilitate complete removal of a liquid from a container, said needle assembly comprising:

a) a base movably disposable exteriorly of the container and including a needle assembly connected thereto, b) said needle assembly comprising a delivery needle including a first portion having an open distal end disposable within the container in fluid communication with the liquid therein, c) said first portion having a sufficient length to extend into and along substantially an entire interior length of the container, d) said delivery needle including a second portion connected to said first portion in substantially transverse relation thereto and disposed exteriorly of the container, said delivery needle further including a first intermediate portion and a second intermediate portion disposed in interconnecting relation with said first and second portions, e) said base including a passage assembly comprising a first opening and a second opening disposed in spaced relation to one another and dimensioned to movably receive said first portion and said second portion therethrough, f) said first opening cooperatively disposed with said first portion to allow passage of said first portion therethrough in an axial direction, g) said second opening cooperatively disposed with said second portion to allow passage of said second portion therethrough in a transverse direction, h) said first and second portions integrally connected to one another and relatively disposed to pass through corresponding ones of said first and second openings, i) a stop structure including a first stop member and a secondary stop member disposed within said passage assembly in spaced relation to one another, j) said first intermediate portion of said delivery needle being movable through and within said passage assembly into and out of movement restricting engagement with said first stop member, k) said second intermediate portion of said delivery needle movable through and within said passage assembly into and out of movement restricting engagement with said secondary stop member, l) said base movable along an axis of said first portion to confronting engagement of a distal end of said first portion with a floor portion of the container, and m) a vent needle fixedly connected to said base and movable with said base relative to the container.

8. A needle assembly as recited in claim 7 further comprising said vent needle fixedly connected to said base in spaced relation to and independently of said delivery needle, said vent needle disposed to define a path of fluid flow between the interior and exterior of the container.

9. A needle assembly as recited in claim 8 further comprising a filter structure disposed adjacent an exterior end of said vent needle and structured to filter fluid passing through said vent needle.

* * * * *